US00PP28978P3

(12) United States Plant Patent
Van Swieten

(10) Patent No.: US PP28,978 P3
(45) Date of Patent: Feb. 20, 2018

(54) ***PHALAENOPSIS* ORCHID PLANT NAMED 'PHALYFREP'**

(50) Latin Name: ***Phalaenopsis* hybrid**
Varietal Denomination: PHALYFREP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 33 days.

(21) Appl. No.: 14/999,658

(22) Filed: Jun. 9, 2016

(65) Prior Publication Data

US 2017/0359935 P1 Dec. 14, 2017

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO: Plant Variety Database, updated on Aug. 9, 2017, citation for 'PHALFPYJA' (1 page).*
EU Community Plant Variety Rights Application No. 2014/2344, Application n°A201404689, filed Sep. 30, 2014, 7 pages.
EU Community Plant Variety Office Official Gazette, 6.2014, Dec. 15, 2014, cover page and pp. 37, 57.
EU Community Plant Variety Rights Certificate on the Grant, No. 41992, issued Nov. 9, 2015, 2 pages.
EU Community Plant Variety Office Official Gazette, 1.2016, Feb. 15, 2016, cover page and p. 80.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALYFREP', particularly characterized by having white flowers with a green-brown lip, 1 to 5 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALYFREP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALYFREP'.

The new *Phalaenopsis* plant is the result of a naturally occurring mutation of *Phalaenopsis* hybrid 'PHALUBIEN' (unpatented) found by the inventor, in Bleiswijk, The Netherlands. The new *Phalaenopsis* plant was discovered by the inventor in August 2010 in a group of plants of the *Phalaenopsis* variety 'PHALUBIEN'. The new *Phalaenopsis* plant has a high number of peduncles and numerous attractive and unique white flowers with a green-brown lip, suitable for potted plant production.

Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 30, 2014. 'PHALYFREP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALYFREP' as a new and distinct variety of *Phalaenopsis* plant.

1) White flowers with a green-brown lip;
2) 1 to 5 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in February 2016. Colors in the photographs may differ from the color values cited in the detailed botanical description, which accurately describe the actual colors of the new variety.

DESCRIPTION OF THE NEW VARIETY

Figure 1:
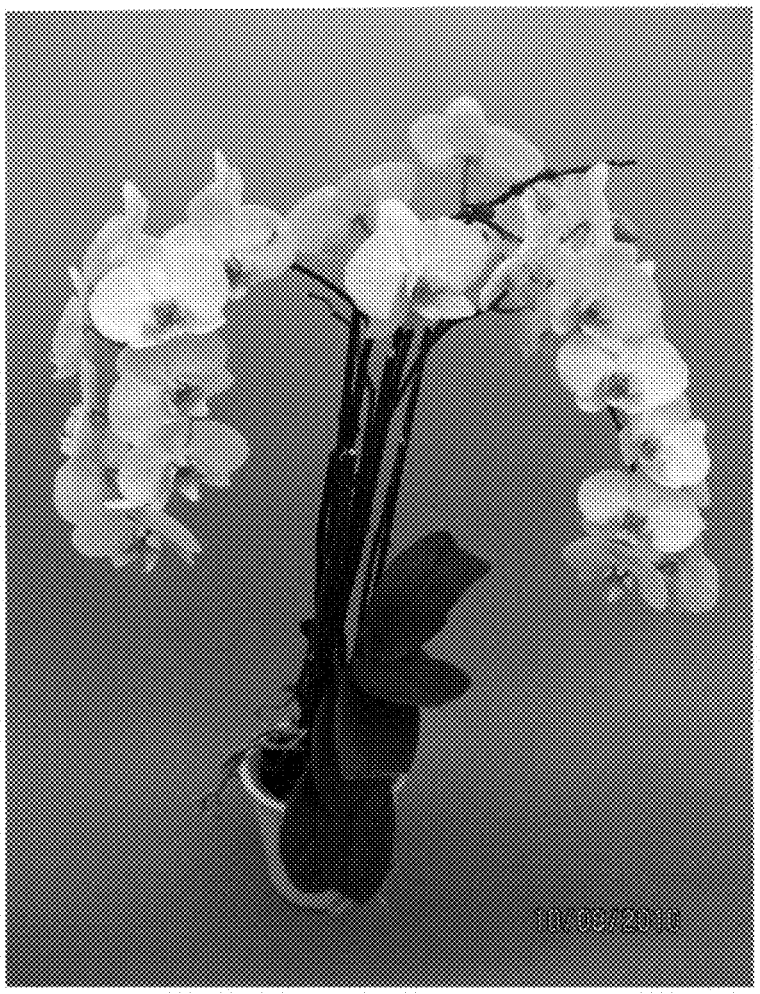
FIG. 1 shows the overall plant habit, including blooms, buds and foliage of 'PHALYFREP'.
Figure 2:
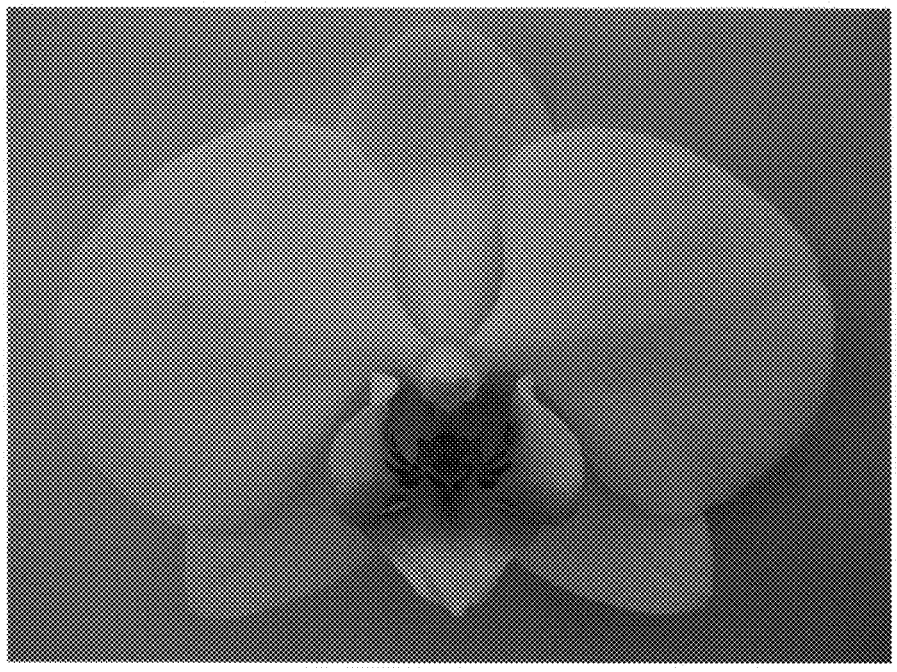
FIG. 2 shows a close-up of a flower of 'PHALYFREP'.
Figure 3:
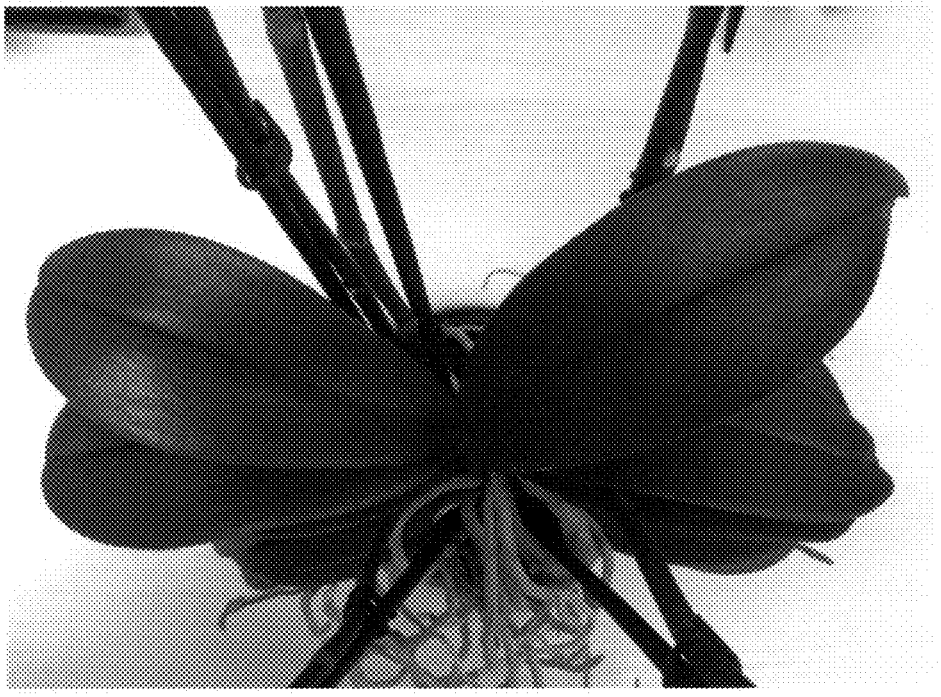
FIG. 3 shows a close-up of the leaves of 'PHALYFREP'.

The following detailed description sets forth the distinctive characteristics of 'PHALYFREP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in February 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—*Phalaenopsis*.
- *Variety name*.—'PHALYFREP'.

Parentage: Naturally occurring mutation of 'PHALUBIEN' (unpatented).

Propagation:
- *Type*.—Meristem tissue culture.

Roots:
- *Root description*.—Greyed-green colored roots with lightly branching lateral roots having light purple colored root tips.

Plant:
- *Commercial crop time to flowering*.—Approximately 48 to 50 weeks from a rooted cutting to finish in a 12 cm pot.
- *Growth habit of peduncle*.—Standard, green leaves, raceme to panicle.
- *Height* (*from soil level to top of inflorescence*).—Approximately 46.0 cm to 56.0 cm.
- *Width* (*measured from leaf tips*).—About 26.0 cm to 30.0 cm.
- *Vigor*.—Strong.

Leaves:
- *Mature leaves*.—Quantity per plant: 9 to 11 leaves are produced before flowering. Length (fully expanded): 13.0 cm to 15.0 cm. Width: 6.0 cm to 7.0 cm. Shape: Oblong. Base shape: Moderately elongated. Apex: Rounded equal. Leaf blade angle with the petiole (measured from the horizontal position): Between 25 degrees and 50 degrees. Leaf margin: Entire. Color: Upper surface: RHS 147A. Lower surface: RHS 146A. Texture: Rough. Thickness: 2.0 mm to 2.2 mm. Venation: Pattern: Parallel. Color of the midvein: Upper surface: RHS 147A. Lower surface: RHS 147B.

Peduncle:
- *Quantity per plant*.—1 to 5.
- *Number of flowers per peduncle*.—9 to 16.
- *Length*.—46.0 cm to 56.0 cm.
- *Diameter*.—5.3 mm to 5.8 mm.
- *Strength*.—Strong.
- *Aspect*.—Upright.
- *Texture*.—Smooth.
- *Color*.—Mix of brown (RHS 200A) with a touch of green (RHS 146B).
- *Internode length*.—40.0 mm to 50.0 mm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 250.0 mm to 270.0 mm.
- *Flowering time*.—First flowers can be expected 10 to 11 months after planting in a 12 cm (diameter) pot.
- *Flower*.—Height: 68.0 mm to 73.0 mm. Diameter: 83.0 mm to 88.0 mm. Depth of lip: 21.0 mm to 23.0 mm.
- *Flower longevity*.—On the plant: 9 to 14 weeks.
- *Fragrance*.—Absent.
- *Flower bud*.—Average size: Large. Length: 23.0 mm to 25.0 mm. Width: 19.0 mm to 21.0 mm. Shape: Egg shaped. Color: Light green (RHS N144D) with a touch of greyed-red (RHS 182B to 182C).
- *Petals*.—Arrangement: Open/free. Shape: Semi-circular. Apex: Emarginated asymmetric. Margin: Entire. Length (from base to tip): 38.0 mm to 40.0 mm. Width: 46.0 mm to 48.0 mm. Color (when fully opened): Upper surface: Basic color: White (RHS NN155D). Over color: Absent. Lower surface: Basic color: White (RHS NN155D). Over color: Light purple (RHS N80D).
- *Dorsal sepal*.—Shape: Elliptic. Apex: Slightly emarginated symmetric. Margin: Entire. Length (from base to tip): 41.0 mm to 43.0 mm. Width: 28.0 mm to 30.0 mm. Color (when fully opened): Upper surface: Basic color: White (RHS NN155D). Over color: Absent. Lower surface: Basic color: White (RHS NN155D). Over color: Light purple (RHS N75D) and diluted green (RHS 145D).
- *Lateral sepals*.—Shape: Ovate. Apex: Obtuse asymmetric. Margin: Entire. Length (from base to tip): 44.0 mm to 46.0 mm. Width: 25.0 mm to 27.0 mm. Color (when fully opened): Upper surface: Basic color: White (RHS NN155D). Over color: Light green at the base and on the lower side of the lateral sepal (RHS 145C), diluted towards the apex (RHS 145D). Lower surface: Basic color: White (RHS NN155D). Over color: Light purple (RHS N75D) and light green (RHS 145C).
- *Labellum* (*lip*).—Margin: Entire. Whiskers: Present. Length of whiskers: 13.0 mm to 15.0 mm. Color of whiskers: White (RHS NN155D). Pubescence on the lip: Absent.
- *Lateral lobe*.—Shape: Spatulate. Length (from base to tip): 20.0 mm to 22.0 mm. Width: 16.0 mm to 18.0 mm. Color: White (RHS NN155D) and green on one side (RHS 154B and 151B) with stripes at the base (RHS 175B and 183B).
- *Apical lobe*.—Shape: Triangular/trullate. Length: 20.0 mm to 22.0 mm. Width: 21.0 mm to 23.0 mm. Color:

White (RHS NN155C) and green (RHS N144B and 151B) with a touch of brown (RHS 175B) at the base.

*Callus*.—Average size: Medium to large. Height: 0.6 cm to 0.7 cm. Length: 0.7 cm to 0.8 cm. Width: 0.5 cm to 0.6 cm. Color: Yellow (RHS 14B); light yellow on the side (RHS 4C) with greyed-orange stripes and dots (RHS 175A).

*Reproductive organs*.—Column: Length: 8.0 mm to 10.0 mm. Diameter: 5.8 mm to 6.0 mm. Color: White (RHS NN155C). Pollinia: Quantity: 2. Diameter: 0.8 mm to 1.0 mm. Color: Orange (RHS N25A). Ovary (part of pedicel with small ribs towards the column): Length: 7.0 mm to 9.0 mm. Diameter: 2.3 mm to 2.5 mm. Pedicel: Length: 31.0 mm to 33.0 mm. Diameter: 2.6 mm to 2.8 mm. Color: Greyed-purple at the base (RHS 187A); mix of light green (RHS 146C and 144D) and light greyed-purple (RHS 186D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALYFREP' differs from the parental variety 'PHALUBIEN' (unpatented) in that 'PHALYFREP' has 9 to 11 leaves present on a 50-week old plant and an average of 1 to 5 branches per plant, whereas 'PHALUBIEN' has 6 to 8 leaves present on a 50-week old plant and an average of 1 to 3 branches per plant. Additionally, 'PHALYFREP' has shorter, narrower leaves than 'PHALUBIEN'.

'PHALYFREP' differs from the commercial variety 'PHALBNIBE' (unpatented) in that 'PHALYFREP' has whiskers with white tips and a weak curvature of the lateral lobe, whereas 'PHALBNIBE' has whiskers with yellow tips and a medium curvature of the lateral lobe. Additionally, 'PHALYFREP' has shorter whiskers and more narrow flowers than 'PHALBNIBE'.

I claim:

1. A new and distinct variety of *Phalaenopsis* plant named 'PHALYFREP', substantially as described and illustrated herein.

* * * * *